`US009675035B2`

United States Patent
Radi et al.

(10) Patent No.: US 9,675,035 B2
(45) Date of Patent: *Jun. 13, 2017

(54) SUNFLOWER MUTANT ALLELE NSMA

(71) Applicant: NUSEED AMERICAS INC., Alsip, IL (US)

(72) Inventors: Scott Arthur Radi, Woodland, CA (US); Erin Marie Gerdes, Fergus Falls, MN (US)

(73) Assignee: NUSEED AMERICAS INC., Alsip, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/092,811

(22) Filed: Apr. 7, 2016

(65) Prior Publication Data

US 2016/0295824 A1 Oct. 13, 2016

Related U.S. Application Data

(60) Provisional application No. 62/145,640, filed on Apr. 10, 2015.

(51) Int. Cl.
| | | |
|---|---|---|
| *A01H 5/10* | (2006.01) | |
| *C12N 15/82* | (2006.01) | |
| *A01H 5/02* | (2006.01) | |
| *C12N 5/14* | (2006.01) | |

(52) U.S. Cl.
CPC .............. *A01H 5/10* (2013.01); *A01H 5/02* (2013.01); *C12N 15/8241* (2013.01); *C12N 15/8274* (2013.01); *C12N 15/8275* (2013.01); *C12N 15/8277* (2013.01); *C12N 15/8278* (2013.01); *C12N 15/8279* (2013.01); *C12N 15/8281* (2013.01); *C12N 15/8282* (2013.01); *C12N 15/8283* (2013.01); *C12N 15/8286* (2013.01); *C12N 15/8289* (2013.01); *C12N 5/14* (2013.01)

(58) Field of Classification Search
None
See application file for complete search history.

(56) References Cited

U.S. PATENT DOCUMENTS

| 5,523,520 A | 6/1996 | Hunsperger et al. |
| 2011/0197297 A1* | 8/2011 | Benson ................ A01H 5/025 |
| | | 800/260 |

FOREIGN PATENT DOCUMENTS

| AR | P160100959 | 4/2016 |
| RU | 2016113514 | 4/2016 |
| UA | A201603799 | 4/2016 |

OTHER PUBLICATIONS

Seeds of Change website (2013).*
Williams 2011 (National Sunflower Variety Review Board Report).*
Seeds of Change website (2013) Archived page can be found at http://web.archive.org/web/20130620055443/http://www.seedsofchange.com/quickfacts.aspx?c=9556&cat=50#ad-image-ProductDetail1_aFirstImage.*
Bowers, et al., 2012, Development of a 10,000 locus genetic map of the sunflower genome based on multiple crosses, G3, 2:721-729.
Burke, et al., 2002, Genetic analysis of sunflower domestication, Genetics, 161:1257-1267.
Eshed, et al., 1996, Less-than-additive epistatic interactions of quantitative trait loci in tomato, Genetics, 143:1807-1817.
Jehan and Lakhanpaul, 2006, Single nucleotide polymorphism (SNP)-Methods and applications in plant genetics: A review, IJBT, 5:435-459.
Kolkman, et al., 2007, Single nucleotide polymorphisms and linkage disequilibrium in sunflower, Genetics, 177:457-468.
Kraft, et al., 2000, Linkage disequilibrium and fingerprinting in sugar beet, Theor. App. Genet., 101:323-326.
Mammadov, et al., 2012, SNP markers and their impact on plant breeding, Int. Journ. Plant Genom., 2012:1-11.
Tang, et al., 2006, Quantitative trait loci for genetically correlated seed traits are tightly linked to branching and pericarp pigment loci in sunflower, Crop Sci. 46:721-734.
Young, et al., 1989, RFLP analysis of the size of chromosomal segments retained around the Tm-2 locus of tomato during backcross breeding, Theor. Appl. Genet., 77:353-359.
Zeven, et al., 1983, Investigation of linkage drag in near isogenic lines of wheat by testing for seedling reaction to races of stem rust, leaf rust and yellow rust, Euphytica, 32:319-327.
U.S. Appl. No. 15/092,835, filed Oct. 13, 2016, Nuseed Americas Inc.
U.S. Appl. No. 15/092,857, filed Oct. 13, 2016, Nuseed Americas Inc.
Williams, D., A Report of the National Sunflower Variety Review Board, Jun. 2011, Association of Official Seed Certifying Agencies, pp. 1-3, 40.

* cited by examiner

Primary Examiner — Matthew Keogh
(74) Attorney, Agent, or Firm — Jondle & Associates, P.C.

(57) ABSTRACT

The present invention relates to a novel mutant allele of sunflower (*Helianthus annuus* L.) designated NSMA, which confers white seed color to sunflower plants. The present invention also relates to plants and seeds of the family or line carrying the NSMA allele. In addition, the present invention is also directed to transferring the NSMA allele to plants in the same species lacking the allele, and is useful for producing novel types and varieties of white-seeded sunflowers.

12 Claims, 5 Drawing Sheets

```
                         SEQUENCE LISTING

<160> NUMBER OF SEQ ID NOS: 4

<210> SEQ ID NO 1
<211> LENGTH: 318
<212> TYPE: DNA
<213> ORGANISM: Helianthus annuus
<220> FEATURE:
<221> NAME/KEY: misc_feature
<222> LOCATION: (244)..(253)
<223> OTHER INFORMATION: n is a, c, g, or t

<400> SEQUENCE: 1
tttctcttat ttctggttaa ttattgtgat ttagtctcta atttcaggtt tattcaataa      60
tgattcggta agctagggtt tagatgatga ttttaatgat ttgttctgat tttttcttca     120
atatcgtgtt cattcgatga tgattcggta acctagggtt tatatgataa attgtatgct     180
gatttcgaat ttcaattgca gatgatcaaa gaagcactgc tagctctgaa cgagaaaggc     240
ggannnnnnn nnnatcttca ggatcgtgtt tatttgatga tgattaggta acctagggtt     300
tatatgatga ttttaatg                                                   318

<210> SEQ ID NO 2
<211> LENGTH: 343
<212> TYPE: DNA
<213> ORGANISM: Helianthus annuus

<400> SEQUENCE: 2
ctccatccat ctccttgaac tgcgtcaaga taacaggaaa gaattataag taaattttcc      60
cacaagtaag ataaaccata gagaatatga gaatccagaa cctgaaagct tgcagcagcc     120
accgtgtcaa gaattttggt tgtggtataa ctgttggact ttaatctaac acgtcttgga     180
ttgatgtcaa cggaactttt ggtccaaaaa gcaaatatat ttgaatccaa tacctataag     240
gcaagatgga attaaaggtt atatttcata catcaatctt taacatggaa cataggtttt     300
ttaattagtt taatgcaata tatttacctc ccactttgtt acg                       343

<210> SEQ ID NO 3
<211> LENGTH: 318
```

```
<212> TYPE: DNA
<213> ORGANISM: Helianthus annuus
<220> FEATURE:
<221> NAME/KEY: misc_feature
<222> LOCATION: (244)..(253)
<223> OTHER INFORMATION: n is a, c, g, or t

<400> SEQUENCE: 3
tttctcttat ttctggttaa ttattgtgat ttagtctcta atttcaggtt tattcaataa      60
tgattcggta agctagggtt tagatgatga ttttaatgat ttgttctgat tttttcttca     120
atatcgtgtt cattcgatga tgattcggta acctagggtt tatatgataa attatatgct    180
gatttcgaat ttcaattgca gatgatcaaa gaagcactgc tagctctgaa cgagaaaggc    240
ggannnnnnn nnnatcttca ggatcgtgtt tatttgatga tgattaggta acctagggtt    300
tatatgatga ttttaatg                                                  318

<210> SEQ ID NO 4
<211> LENGTH: 343
<212> TYPE: DNA
<213> ORGANISM: Helianthus annuus

<400> SEQUENCE: 4
ctccatccat ctccttgaac tgcgtcaaga taacaggaaa gaattataag taaattttcc     60
cacaagtaag ataaaccata gagaatatga gaatccagaa cctgaaagct tgcagcagcc   120
accgtgtcaa gaattttggt tgtggtataa ctgttggact ttaatctaac acgtcttgga   180
ttgatgtcaa cggaactttt ggtccaaaaa gcaaatatat ttgaatccaa tacctataag   240
gcaagatgga attaaaggtt atatttcata catcgatctt taacatggaa cataggtttt   300
ttaattagtt taatgcaata tatttacctc ccactttgtt acg                     343
```

SUNFLOWER MUTANT ALLELE NSMA

CROSS REFERENCE TO RELATED APPLICATIONS

This application claims the benefit of priority from U.S. provisional patent application Ser. No. 62/145,640 filed on Apr. 10, 2015, which is incorporated herein by reference in its entirety.

BACKGROUND OF THE INVENTION

The present invention relates to a mutant allele of sunflower designated NSMA, which confers white seed color. The present invention also relates to sunflower plants, plant parts and seeds having the NSMA mutant allele. In addition, the present invention is also directed to transferring the NSMA allele to plants in the same species lacking the allele, and is useful for producing novel plants and varieties of sunflower having white seeds. All publications cited in this application are herein incorporated by reference.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include increased head size and weight, higher seed yield, improved color, resistance to diseases and insects, tolerance to drought and heat, and better agronomic quality.

The cultivated sunflower (*Helianthus annuus* L.) is a major worldwide source of vegetable oil. In the United States, the major sunflower producing states are the Dakotas, Minnesota, Kansas, Colorado, Nebraska, Texas and California, although most states have some commercial acreage.

Sunflowers are considered oilseeds, along with cottonseed, soybeans and canola and the growth of sunflower as an oilseed crop has rivaled that of soybean. The oil accounts for 80% of the value of the sunflower crop, as contrasted with soybean which derives most of its value from the meal. Sunflower oil is generally considered a premium oil because of its light color, high level of unsaturated fatty acids, lack of linolenic acid, bland flavor and high smoke points. The primary fatty acids in the oil are oleic and linoleic with the remainder consisting of palmitic and stearic saturated fatty acids.

Non-dehulled or partly dehulled sunflower meal has been substituted successfully for soybean meal in isonitrogenous (equal protein) diets for ruminant animals, as well as for swine and poultry feeding. Sunflower meal is higher in fiber, has a lower energy value and is lower in lysine but higher in methionine than soybean meal. Protein percentage of sunflower meal ranges from 28% for non-dehulled seeds to 42% for completely dehulled seeds.

In addition to its use in food and food products for humans and animals, sunflower oil also has industrial uses. It has been used in paints, varnishes and plastics because of good semidrying properties without the color modification associated with oils high in linolenic acid. It has also been used in the manufacture of soaps, detergents and cosmetics. The use of sunflower oil (and other vegetable oils) as a pesticide carrier, and in the production agrichemicals, surfactants, adhesives, fabric softeners, lubricants and coatings has been explored. Considerable work has also been done to explore the potential of sunflower as an alternate fuel source in diesel engines because sunflower oil contains 93% of the energy of US Number 2 diesel fuel (octane rating of 37). Sunflower oil has also been proposed as a source of hydrogen for hydrogen fuel cells. (BBC News, Aug. 26, 2004).

Sunflower is an annual, erect, broadleaf plant with a strong taproot and a prolific lateral spread of surface roots. Stems are usually round early in the season, angular and woody later in the season, and normally unbranched. The sunflower head is not a single flower (as the name implies) but is made up of 1,000 to 2,000 individual flowers joined at a common receptacle. The flowers around the circumference are ligulate ray flowers without stamens or pistils; the remaining flowers are perfect flowers with stamens and pistils. Anthesis (pollen shedding) begins at the periphery and proceeds to the center of the head. Since many sunflower varieties have a degree of self-incompatibility, pollen movement between plants by insects is important, and bee colonies have generally increased yields.

There are two basic types of sunflowers grown in North America: 1) oil-type sunflower used for oilseed production and 2) non-oilseed, or confectionery sunflower, used for food and birdseed. Oilseed sunflower seeds are usually smaller and black in color, whereas non-oilseed or confectionery sunflower seeds are larger than oilseed and are black and white striped.

At least 30 diseases, caused by various fungi, bacteria and viruses, have been identified on wild or cultivated sunflower, but only a few are of economic significance as far as causing yield losses. The sunflower diseases *Phoma* Black Stem (*Phoma macdonaldii*), *Phomopsis* Stem Canker (*Phomopsis helianthi*), *Verticillium* Leaf Mottle (*Verticillium dahliae*) and *Sclerotinia* (*Sclerotinia sclerotiorum*) are some of the most significant disease problems in sunflower producing areas of China, United States and Europe.

The development of a cytoplasmic male-sterile and restorer system for sunflower has enabled seed companies to produce high-quality hybrid seed. Most of these have higher yields than open-pollinated varieties and are higher in percent oil. Performance of varieties tested over several environments is the best basis for selecting sunflower hybrids. The choice should consider yield, oil percentage, maturity, seed size (for non-oilseed markets), and lodging and disease resistance.

Therefore, it is desirable to develop new sunflower types with excellent seed characteristics, such as novel confectionery sunflower seeds that are white seeded, as conferred by mutant allele of sunflower designated NSMA. It is especially desirable to have a dominant allele conferring white seed color to sunflower that is easy to transfer to different genetic backgrounds and have expression of white seed color in hybrid sunflower combinations and their progeny. A unique confectionary sunflower seed color, such as white, aids with seed sorting and breeding. Further, certain consumers find white sunflower seeds more desirable than the black and white striped confectionary sunflower seeds currently available in the market.

The foregoing examples of the related art and limitations related therewith are intended to be illustrative and not exclusive. Other limitations of the related art will become apparent to those of skill in the art upon a reading of the specification.

SUMMARY OF THE INVENTION

The following embodiments and aspects thereof are described in conjunction with systems, tools, and methods which are meant to be exemplary and illustrative, not limiting in scope. In various embodiments, one or more of the above-described problems have been reduced or eliminated, while other embodiments are directed to other improvements.

According to the present invention, there is provided a novel mutant allele of sunflower designated NSMA that confers white seed color in a dominant fashion to sunflower plants. This invention thus relates to mutant allele NSMA, to sunflower seeds and plants having mutant allele NSMA, sunflower varieties and hybrids having mutant allele NSMA, and to a method for producing a sunflower plant having mutant allele NSMA. In another aspect of the present invention, the dominant white trait conferred by mutant allele NSMA when carried in an inbred female sunflower line offers the unique ability to directly use any elite male sunflower to make a white seeded hybrid sunflower. Another aspect of the invention relates to any sunflower seed, plant or part thereof, having mutant allele NSMA.

The invention also provides methods for introducing the mutant allele of the present invention into different plants by crossing a plant which lacks the mutant allele with a plant that has allele NSMA, selfing the resulting generations and then selecting for plants exhibiting white seed color. The invention further relates to the creation of variants by mutagenesis or transformation of sunflower varieties having mutant allele NSMA.

Another embodiment of the invention is to provide methods for producing other sunflower plants containing the mutant allele NSMA. Sunflower cultivars derived by the use of those methods are also part of the invention.

In another aspect, the present invention provides regenerable cells for use in tissue culture of sunflower plants having mutant allele NSMA. The tissue culture will preferably be capable of regenerating plants having the physiological and morphological characteristics of the foregoing sunflower plant, and of regenerating plants having substantially the same genotype as the foregoing sunflower plant. Preferably, the regenerable cells in such tissue cultures will be embryos, protoplasts, meristematic cells, callus, pollen, cotyledon, leaves, flowers, anthers, roots, pistils, root tips, glumes, seeds, panicles or stems. Still further, the present invention provides sunflower plants regenerated from the tissue cultures of the invention.

The invention further provides for a sunflower plant having mutant allele NSMA having white seeds.

In addition to the exemplary aspects and embodiments described above, further aspects and embodiments will become apparent by reference by study of the following descriptions.

SUMMARY OF THE SEQUENCE LISTING

Figure 1:
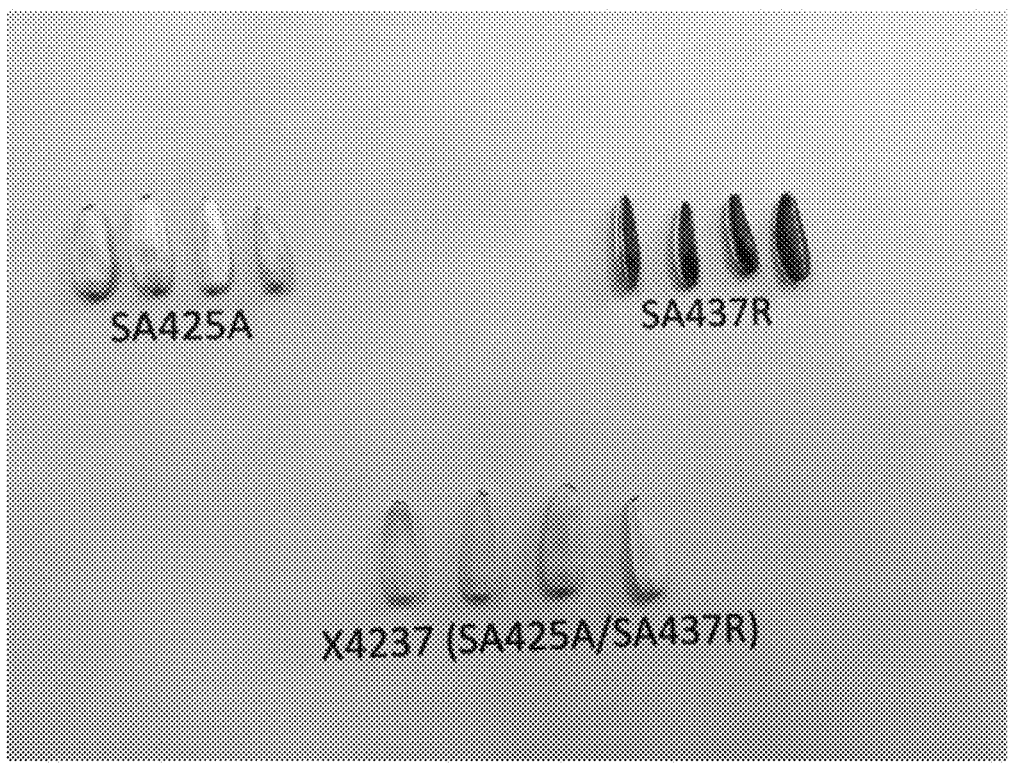
FIG. 1 shows a photo of seeds of hybrid sunflower X4237 (white), and its parents, inbred sunflower SA425A (white), which contains mutant allele NSMA, and sunflower SA437R (black). Hybrid sunflower X4237 has white seed color conferred by mutant allele NSMA.

The present application is being filed along with a Sequence Listing in electronic format. The Sequence Listing is entitled SequenceListing_ST25.txt, was created on 4 Apr. 2016 and is 3 kb in size. The information in the electronic format of the Sequence Listing is part of the present application and is incorporated herein by reference in its entirety.

SEQ ID NO:1 sets forth the sequence of the SNP marker NHA006022 for white-seeded sunflower SA425A containing mutant allele NSMA having nucleotide 'G' at position 174.

SEQ ID NO:2 sets forth the sequence of the SNP marker NHA006025 for white-seeded sunflower SA425A containing mutant allele NSMA having nucleotide 'A' at position 275.

SEQ ID NO:3 sets forth the sequence of the SNP marker NHA006022 for gray-seeded sunflower 10CR584 having nucleotide 'A' at position 174.

SEQ ID NO:4 sets forth the sequence of the SNP marker NHA006025 for gray-seeded sunflower 10CR584 having nucleotide 'G' at position 275.

DETAILED DESCRIPTION OF THE INVENTION

In the description and tables which follow, a number of terms are used. In order to provide a clear and consistent understanding of the specification and claims, including the scope to be given such terms, the following definitions are provided:

Abiotic stress. As used herein, abiotic stress relates to all non-living chemical and physical factors in the environment. Examples of abiotic stress include, but are not limited to, drought, flooding, salinity, temperature, and climate change.

Allele. The allele is any of one or more alternative forms of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Cell. Cell as used herein includes a plant cell, whether isolated, in tissue culture or incorporated in a plant or plant part.

Cotyledon. One of the first leaves of the embryo of a seed plant; typically one or more in monocotyledons, two in dicotyledons, and two or more in gymnosperms.

Dominant trait or dominant allele. As used herein in regards to mutant allele NSMA, means dominant or partially dominant and expressed in many genetic backgrounds.

Essentially all the physiological and morphological characteristics. A plant having essentially all the physiological and morphological characteristics means a plant having the physiological and morphological characteristics of the recurrent parent, except for the characteristics derived from the converted gene.

$F_\#$. The "F" symbol denotes the filial generation, and the # is the generation number, such as $F_1$, $F_2$, $F_3$, etc.

Gene. As used herein, "gene" refers to a segment of nucleic acid. A gene can be introduced into a genome of a species, whether from a different species or from the same species, using transformation or various breeding methods.

Genetically Modified. Describes an organism that has received genetic material from another, or had its genetic material modified, resulting in a change in one or more of its phenotypic characteristics. Methods used to modify, introduce or delete the genetic material may include mutation breeding, backcross conversion, genetic transformation, single and multiple gene conversion, and/or direct gene transfer.

Genotype. Refers to the genetic constitution of a cell or organism.

Length/Width (L/W) Ratio. This ratio is determined by dividing the average length (L) by the average width (W).

Linkage. Refers to a phenomenon wherein alleles on the same chromosome tend to segregate together more often than expected by chance if their transmission was independent.

Linkage Disequilibrium. Refers to a phenomenon wherein alleles tend to remain together in linkage groups when segregating from parents to offspring, with a greater frequency than expected from their individual frequencies.

Locus. A locus confers one or more traits such as, for example, male sterility, herbicide tolerance, insect resistance, disease resistance, waxy starch, modified fatty acid metabolism, modified phytic acid metabolism, modified carbohydrate metabolism and modified protein metabolism. The trait may be, for example, conferred by a naturally occurring gene introduced into the genome of the variety by backcrossing, a natural or induced mutation, or a transgene introduced through genetic transformation techniques. A locus may comprise one or more alleles integrated at a single chromosomal location.

Marker-assisted selection (MAS). Also called marker-assisted breeding. The use of DNA markers that are tightly-linked to target loci as a substitute for or to assist phenotypic screening. Ideally, the marker used for selection associates at high frequency with the gene or quantitative trait locus of interest, due to genetic linkage. Marker loci that are tightly linked to major genes can be used for selection and are sometimes more efficient than direct selection for the target gene.

Multiple Gene Converted (Conversion). Multiple gene converted (conversion) includes plants developed by a plant breeding technique called backcrossing wherein essentially all of the desired morphological and physiological characteristics of an inbred are recovered, while retaining two or more genes transferred into the inbred via crossing and backcrossing. The term can also refer to the introduction of multiple genes through genetic engineering techniques known in the art.

NSMA. Refers to the novel mutant allele of the present invention that confers white seed color in a dominant fashion. NSMA is found in inbred sunflower SA425A, sunflower hybrid X4237, as well as in over 49 other different genetic backgrounds, as shown in Table 1 and the Examples. The white seed color gene NSMA was identified as a single gene that underlies the seed color regulation and was mapped to an interval of 5.2 centimorgan (cM) on the long arm of linkage group LG16 in sunflower and was tightly linked to flanking SNP markers NHA006022 (SEQ ID NO:1) and NHA006025 (SEQ ID NO:2).

Percent Identity. Percent identity as used herein refers to the comparison of the homozygous alleles of two sunflower varieties. Percent identity is determined by comparing a statistically significant number of the homozygous alleles of two developed varieties. For example, a percent identity of 90% between sunflower variety 1 and sunflower variety 2 means that the two varieties have the same allele at 90% of their loci.

Percent Similarity. Percent similarity as used herein refers to the comparison of the homozygous alleles of a sunflower variety with another sunflower plant, and if the homozygous allele of both sunflower plants matches at least one of the alleles from the other plant then they are scored as similar. Percent similarity is determined by comparing a statistically significant number of loci and recording the number of loci with similar alleles as a percentage. A percent similarity of 90% between the sunflower plant of this invention and another plant means that the sunflower plant of this invention matches at least one of the alleles of the other sunflower plant at 90% of the loci.

Plant. As used herein, the term "plant" includes reference to an immature or mature whole plant, including a plant from which seed or grain or anthers have been removed. Seed or embryo that will produce the plant is also considered to be the plant.

Plant Height. Plant height in centimeters is taken from soil surface to the tip at harvest.

Plant Parts. As used herein, the term "plant parts" (or a soybean plant, or a part thereof) includes but is not limited to protoplasts, leaves, stems, roots, root tips, anthers, pistils, seed, grain, embryo, pollen, ovules, cotyledon, hypocotyl, pod, flower, shoot, tissue, petiole, cells, meristematic cells, and the like.

Pubescence. This refers to a covering of very fine hairs closely arranged on the leaves, stems and glumes of the plant.

Quantitative Trait Loci. Quantitative Trait Loci (QTL) refers to genetic loci that control to some degree, numerically representable traits that are usually continuously distributed.

Regeneration. Regeneration refers to the development of a plant from tissue culture.

RHS. RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

Rogueing. Rogueing is the process in seed production where undesired plants are removed from a variety. The plants are removed since they differ physically from the general desired expressed characteristics of the variety. The differences can be related to size, color, maturity, leaf texture, leaf margins, growth habit, or any other characteristic that distinguishes the plant.

Single gene converted. Single gene converted or conversion or locus conversion plant refers to plants which are developed by a plant breeding technique called backcrossing or via genetic engineering wherein essentially all of the desired morphological and physiological characteristics of a line are recovered in addition to the single gene transferred into the line via the backcrossing technique or via genetic engineering.

SNP. Refers to single nucleotide polymorphisms. Variation at a single position in a DNA sequence among individuals; SNPs are usually considered to be point mutations that have been evolutionarily successful enough to recur in a significant proportion of the population of a species. If an SNP occurs within a gene, then the gene is described as having more than one allele. SNPs can also occur in non-coding regions of DNA. If certain SNPs are known to be associated with a trait, then stretches of DNA near the SNPs can be examined in an attempt to identify the gene or genes responsible for the trait.

Sunflower. Helianthus annuus L., as used herein, sunflower includes confectionery, oilseed (oil-type) and conoil sunflower types. Conoil sunflower refers to sunflower hybrids developed using both oil-type and confection parentage. Conoils tend to have higher oil content than traditional confection varieties.

White-seeded or white seed color. As used herein in describing the present invention, refers to the white sunflower seed color conferred by mutant allele NSMA, which is found in inbred sunflower SA425A, sunflower hybrid X4237, as well as in over 49 other different genetic backgrounds, as shown in Table 1 and the Examples and Figures. The white seed color includes, but is not limited to, the following RHS colors depending on the genetic background and environment: RHS 155A-D, N155A-D, 156A-D, 157A-D, 158A-D, and 159A-D.

Sunflower mutant allele NSMA of the present invention confers white seed color to sunflowers. The white seed color gene NSMA was identified as a single gene that underlies the seed color regulation and was mapped to an interval of 5.2 centimorgan (cM) on the long arm of linkage group LG16 in sunflower, which is surprising because seed color is typically controlled by several genes. Previously, there were no known sunflower plants having a dominant allele for white seed color. The white seed color gene NSMA mapping results presented herein will greatly facilitate white seed sunflower breeding through marker-assisted breeding.

Additionally, it is desirable to have a dominant allele conferring white seed color to sunflower, such as mutant allele NSMA, which is easy to transfer to different genetic backgrounds and confers expression of white seed color in hybrid sunflower combinations and their progeny. A unique confectionary sunflower seed color, such as white, aids with seed sorting and breeding. Further, certain consumers find white sunflower seeds more desirable than the black and white striped or gray confectionary sunflower seeds currently available in the market.

Mutant allele NSMA of the present invention unexpectedly arose in the inventors' research program in a selection from the cross of an unknown predominately white seeded female open-pollinated (OP) sunflower and a male sunflower having black seeds with stripes. When sunflowers containing NSMA are used in crosses, the resulting hybrid sunflowers have white seed color conferred by mutant allele NSMA.

This invention is also directed to methods for producing a sunflower plant by crossing a first parent sunflower plant with a second parent sunflower plant, wherein the first parent sunflower plant or second parent sunflower plant is the sunflower plant having mutant allele NSMA. Further, both the first parent sunflower plant and second parent sunflower plant may have mutant allele NSMA. Therefore, any methods using sunflowers having mutant allele NSMA are part of this invention: selfing, backcrosses, hybrid breeding, and crosses to populations. Any plants produced using plants having mutant allele NSMA as at least one parent are within the scope of this invention.

As used herein, the term plant includes plant cells, plant protoplasts, plant cell tissue cultures from which sunflower plants can be regenerated, plant calli, plant clumps and plant cells that are intact in plants, or parts of plants, such as embryos, protoplasts, meristematic cells, callus, pollen, cotyledon, leaves, flowers, anthers, roots, pistils, root tips, glumes, seeds, panicles or stems, and the like.

EXAMPLES

Example 1. Discovery of Sunflower Mutant Allele NSMA

Mutant allele NSMA of the present invention unexpectedly arose in the inventors' research program in a selection from the cross of an unknown predominately white seeded female open-pollinated (OP) sunflower and a male sunflower having black seeds with stripes.

Example 2. Transferring Mutant Allele NSMA into Various Genetic Backgrounds

Unexpectedly, the novel genetic factor of the present invention, which has been designated NSMA, is capable of transmitting white seed color when sunflower plants containing NSMA are crossed with sunflower plants lacking the mutant allele NSMA. Mutant allele NSMA is believed to be a novel dominant allele that may have additional modifier genes. It is a feature of the present invention that mutant allele NSMA may be used in and transferred among various sunflower plants.

Mutant allele NSMA is advantageous for use in breeding because the dominant trait only needs to be carried in one parent. Without the dominant trait, it would be difficult to develop white male and female sunflower inbreds with other important traits due to the large number of genes in both parents.

$F_2$ selections across various populations that used inbred sunflower SA425A, which contains mutant allele NSMA and has white seed color, as a parent have been checked for white seed color. In one example, the segregation patterns of this material showed 53 white seeds out of 77 total, which fits the expected 3:1 pattern of a dominant trait.

Example 3. Transferring Mutant Allele NSMA into Hybrid Sunflower X4237

Inbred sunflower designated SA425A, which has white seed color and contains mutant allele NSMA, was crossed to a black-seeded sunflower, designated SA437R, to produce hybrid sunflower X4237. Hybrid sunflower X4237 has white seed color conferred by mutant allele NSMA. The seeds of SA425A (white), SA437R (black) and hybrid X4237 (white) are shown in FIG. 1.

Example 4. Transferring Mutant Allele NSMA into Hybrid Sunflower SA425A/SA438R

Figure 2:
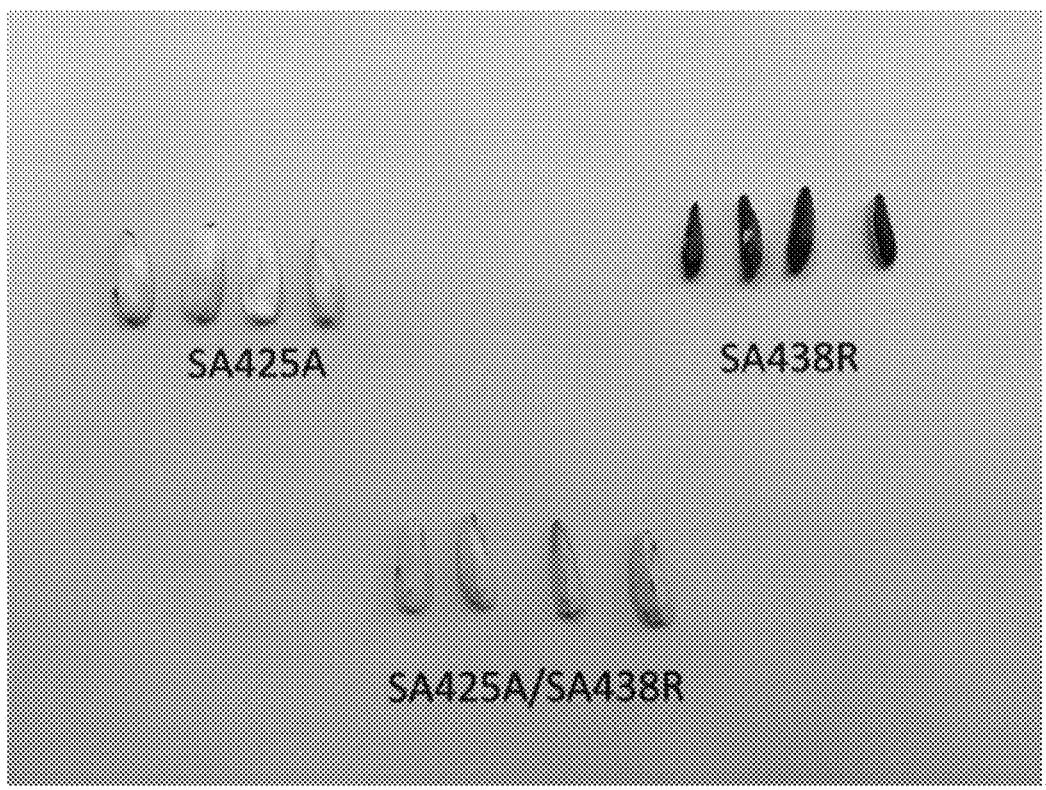
FIG. 2 shows a photo of seeds of hybrid sunflower SA425A/SA438R (white) and its parents, inbred sunflower SA425A (white), which contains mutant allele NSMA, and sunflower SA438R (black). Hybrid sunflower SA425A/SA438R has white seed color conferred by mutant allele NSMA.

Inbred sunflower designated SA425A, which has white seed color and contains mutant allele NSMA, was crossed to a black-seeded sunflower, designated SA438R, to produce hybrid sunflower SA425A/SA438R. Hybrid sunflower SA425A/SA438R has white seed color conferred by mutant allele NSMA. The seeds of SA425A (white), SA438R (black) and hybrid SA425A/SA438R (white) are shown in FIG. 2.

Example 5. Transferring Mutant Allele NSMA into Hybrid Sunflower SA425A/11CR59

Figure 3:
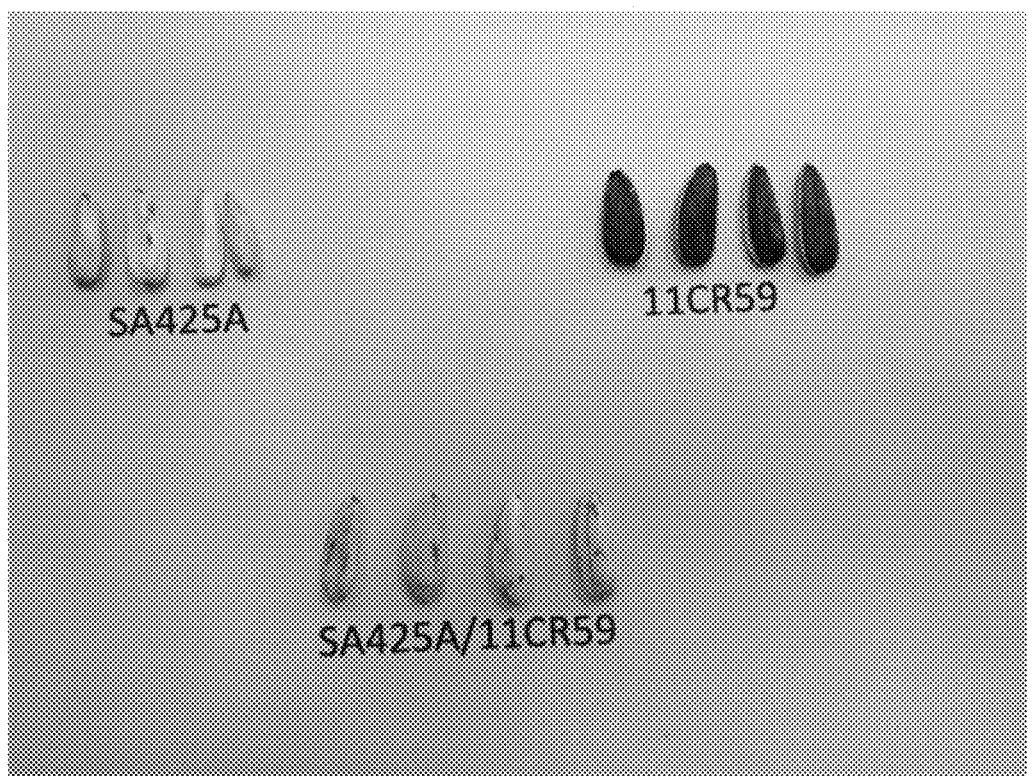
FIG. 3 shows a photo of seeds of hybrid sunflower SA425A/11CR59 (white) and its parents, inbred sunflower SA425A (white), which contains mutant allele NSMA, and sunflower 11CR59 (black). Hybrid sunflower SA425A/11CR59 has white seed color conferred by mutant allele NSMA.

Inbred sunflower designated SA425A, which has white seed color and contains mutant allele NSMA, was crossed to a black-seeded sunflower, designated 11CR59, to produce hybrid sunflower SA425A/11CR59. Hybrid sunflower SA425A/11CR59 has white seed color conferred by mutant allele NSMA. The seeds of SA425A (white), 11CR59 (black) and hybrid SA425A/11CR59 (white) are shown in FIG. 3.

Example 6. Verifying the Presence of Mutant Allele NSMA

In order to determine whether a white sunflower seed contains mutant allele NSMA, test crosses are made to black or traditional lines and then the resulting $F_1$ hybrids are grown. A cross that contained mutant allele NSMA will produce white seed, whereas a cross with, for example, a white seeded open-pollinated (OP) variety would produce striped, gray or black seed. Additionally, genetic markers may be used to identify mutant allele NSMA and plants containing NSMA, such as SNP markers NHA006022 (SEQ ID NO:1) and NHA006025 (SEQ ID NO: 2).

Example 7. Additional Hybrid Sunflowers Containing Mutant Allele NSMA

Table 1 shows 49 sunflower $F_1$ hybrids having white seed color and containing mutant allele NSMA that have been tested using inbred sunflower SA425A as the female parent. The male parents used span a wide range of confection sunflower genetics and most had traditional color and striping of confection sunflowers, meaning black seeds with predominantly marginal white stripes. A few of the males used in the crosses were mostly white with some striping.

Table 1, column 1 shows the hybrid sunflower name, column 2 shows the pedigree, column 4 shows the female parent, column 5 shows the male parent and column 6 shows the seed color of the $F_1$ hybrid sunflower.

TABLE 1

| Name | Pedigree | Female Parent | Male Parent | $F_1$ Seed Color |
| --- | --- | --- | --- | --- |
| NHW12822 | SA425A/10CR584 | SA425A | 10CR584 | White |
| NHW130222 | SA425A/11CR101 | SA425A | 11CR101 | White |
| NHW130223 | SA425A/11CR103 | SA425A | 11CR103 | White |
| NHW130224 | SA425A/11CR112 | SA425A | 11CR112 | White |
| NHW130247 | SA425A/11CR113 | SA425A | 11CR113 | White |
| NHW130225 | SA425A/11CR119 | SA425A | 11CR119 | White |
| NHW130226 | SA425A/11CR129 | SA425A | 11CR129 | White |
| NHW130227 | SA425A/11CR13 | SA425A | 11CR13 | White |
| NHW130228 | SA425A/11CR136 | SA425A | 11CR136 | White |
| NHW130229 | SA425A/11CR150 | SA425A | 11CR150 | White |
| NHW130249 | SA425A/11CR156 | SA425A | 11CR156 | White |
| NHW130230 | SA425A/11CR16 | SA425A | 11CR16 | White |
| NHW130231 | SA425A/11CR17 | SA425A | 11CR17 | White |
| NHW130232 | SA425A/11CR18 | SA425A | 11CR18 | White |
| NHW130233 | SA425A/11CR251 | SA425A | 11CR251 | White |
| NHW130234 | SA425A/11CR253 | SA425A | 11CR253 | White |
| NHW130235 | SA425A/11CR255 | SA425A | 11CR255 | White |
| NHW130236 | SA425A/11CR27 | SA425A | 11CR27 | White |
| NHW130250 | SA425A/11CR293 | SA425A | 11CR293 | White |
| NHW130251 | SA425A/11CR351 | SA425A | 11CR351 | White |
| NHW130252 | SA425A/11CR401 | SA425A | 11CR401 | White |
| NHW130237 | SA425A/11CR356 | SA425A | 11CR409 | White |
| NHW130238 | SA425A/11CR409 | SA425A | 11CR409 | White |
| NHW130239 | SA425A/11CR50 | SA425A | 11CR50 | White |
| NHW130240 | SA425A/11CR59 | SA425A | 11CR59 | White |
| NHW130241 | SA425A/11CR63 | SA425A | 11CR63 | White |
| NHW130242 | SA425A/11CR68 | SA425A | 11CR68 | White |
| NHW130243 | SA425A/11CR85 | SA425A | 11CR85 | White |
| NHW130244 | SA425A/11CR94 | SA425A | 11CR94 | White |
| NHW130245 | SA425A/11CR95 | SA425A | 11CR95 | White |
| NSKM44628 | SA425A/K13SM54R | SA425A | K13SM54R | White |
| NLWM43203 | SA425A/K13SM62R | SA425A | K13SM62R | White |
| NSKM44639 | SA425A/SA422R | SA425A | SA422R | White |
| NJKM53722 | SA425A/SA423R | SA425A | SA423R | White |
| NSK12M131 | SA425A/SA431R | SA425A | SA431R | White |
| NSKM44657 | SA425A/SA434R | SA425A | SA434R | White |
| X4237 | SA425A/SA437R | SA425A | SA437R | White |
| NSK13M330 | SA425A/SA438R | SA425A | SA438R | White |
| NLWM43204 | SA425A/SA451R | SA425A | SA451R | White |
| NLWM43041 | SA425A/WSM4501R | SA425A | WSM4501R | White |
| NLWM43042 | SA425A/WSM4519R | SA425A | WSM4519R | White |
| NLWM43043 | SA425A/WSM4522R | SA425A | WSM4522R | White |
| NLWM43044 | SA425A/WSM4533R | SA425A | WSM4533R | White |
| NLWM43045 | SA425A/WSM4543R | SA425A | WSM4543R | White |
| NLWM43046 | SA425A/WSM4544R | SA425A | WSM4544R | White |
| NLWM43047 | SA425A/WSM4547R | SA425A | WSM4547R | White |
| NLWM43048 | SA425A/WSM4554R | SA425A | WSM3804R | White |
| NLWM43049 | SA425A/WSM4559R | SA425A | WSM4559R | White |

As shown in Table 1, mutant allele NSMA is transferable to different genetic backgrounds, and all hybrid combinations using SA425A as a parent have white seed color and contain mutant allele NSMA.

Example 8. Genetic Mapping of NSMA White Seed Color Gene in Sunflower

The seed color of sunflower (*Helianthus annuus* L.) cytoplasmic male sterile (CMS) line SA425A is white as conferred by mutant allele NSMA, while the seed color of male fertility restorer line 10CR584 is gray. To map the gene underlying the white seed color, one $F_2$ mapping population of 180 plants was generated from the cross between sunflowers SA425A and 10CR584. The mapping population was planted in the greenhouse facility of Nuseed Americans in Woodland, Calif., on Feb. 16, 2015. The mature seeds were harvested from individual plant, dried and then recorded the color through visual inspection.

Fresh leaf samples were collected from each $F_2$ plant and DNA was isolated. Single nucleotide polymorphism (SNP) markers were used to genotype the mapping population. Sequences that were used for developing markers were mined from public domain through a bioinformatics approach. The SNP markers were analyzed on LGC KASP genotyping platform (http://www.lgcgroup.com/products/kasp-genotyping-chemistry/). The genotyping data was processed using the Kraken software of LGC. Mapping software JoinMap (version 4.1) was used to generate the genetic map of the white color gene region and MapQTL (version 6) was adopted to conduct the linkage analysis between the color phenotypes and marker genotypes.

In the $F_2$ mapping population of 180 plants, 136 of them were identified to have white color seed while the other 42 plants had gray seed color. No data was obtained for two plants. Chi-square test showed that the segregation of white color to gray color fit a ratio of 3:1 ($\chi^2(3:1)=0.187$, P>0.05) which indicated that a single gene underlies the seed color regulation. The white color is a dominant trait while the gray color is a recessive trait.

Since a single gene was determined to control the seed color, the gene underlying the white color was mapped by candidate gene approach instead of conducting whole genome association mapping. Seed color related genes were previously reported on the long arms of sunflower linkage group (LG) 16 and 17 (Tang et al., 2006). A small subset of mapping population including 10 plants with white color, 10 plants with gray color and parents were used to conduct initial marker polymorphism screening and association analysis. Three polymorphic markers NHA002903, NHA002966, and NHA003004 on LG16 were found to have some level of association with the seed color. Then these three markers were used to genotype the whole $F_2$ mapping population. Linkage analysis indicated that these three markers were linked with the white color gene and located on one side of the gene.

Figure 4:
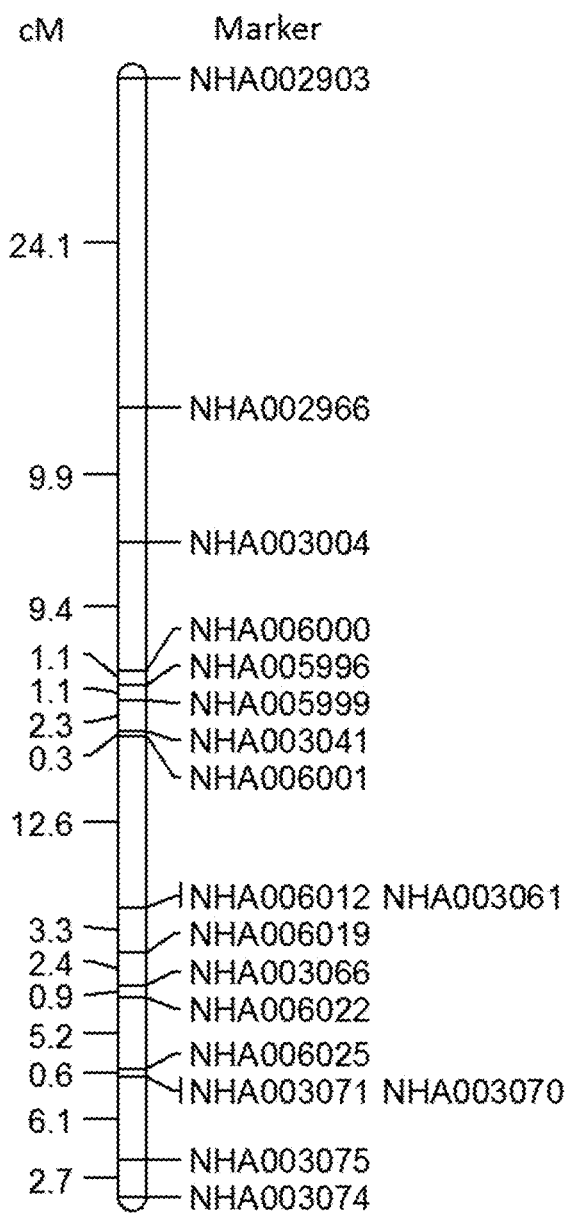
FIG. 4 shows a genetic map of the white seed color gene region on the long arm of sunflower linkage group (LG) 16. The white seed color gene was mapped to an interval of 5.2 centimorgan (cM) on LG16 and was flanked by SNP markers NHA006022 and NHA006025.
Figure 5:
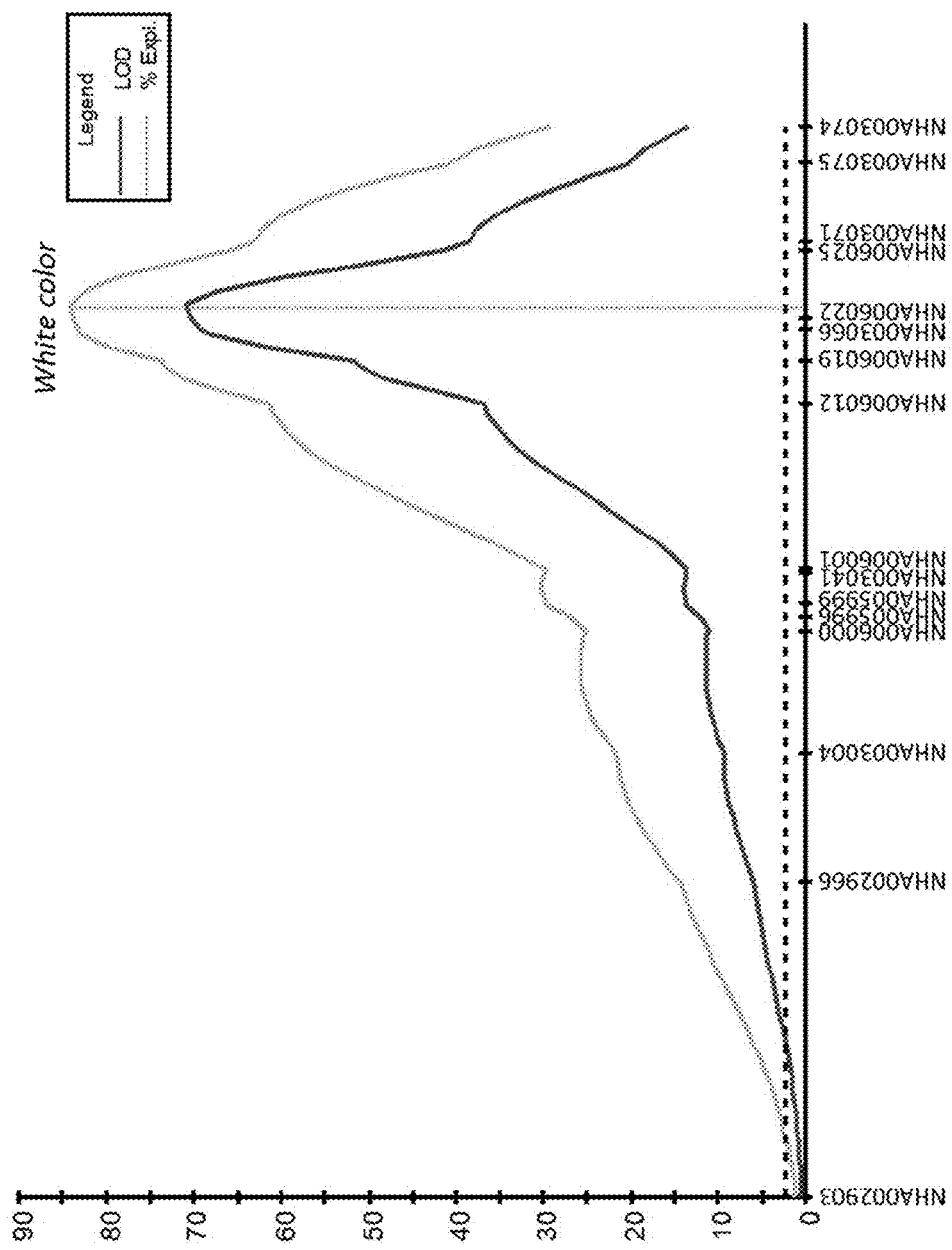
FIG. 5 shows the mapping results of the white seed color gene on LG16 in sunflower.

After the white color gene was initially mapped onto the long arm of LG16, additional SNP markers of the region were screened for polymorphism. In total, 15 more polymorphic SNP markers were identified. Then the newly identified markers were used to genotype the mapping population. The genetic map of the region was generated using mapping software JoinMap (FIG. 4). Linkage analysis between the genotypes and phenotypes was conducted using gene mapping software MapQTL (FIG. 5).

As shown in FIG. 4, the white seed color gene was mapped to an interval of 5.2 centimorgan (cM) on LG16 and was tightly linked to flanking SNP markers NHA006022 (SEQ ID NO:1) and NHA006025 (SEQ ID NO:2). For marker NHA006022, white seeded sunflower SA425A containing mutant allele NSMA has an SNP with nucleotide 'G' in its DNA sequence at nucleotide 174 in SEQ ID NO:1, whereas the gray seed color parent 10CR584 has an SNP with nucleotide 'A' in the same position on NHA006022 (SEQ ID NO:3). Similarly, for marker NHA006025, white seeded sunflower SA425A containing mutant allele NSMA has an SNP with nucleotide 'A' in its DNA sequence at nucleotide 275 in SEQ ID NO:2, whereas the gray seed color parent 10CR584 has an SNP with nucleotide 'G' in the same position on NHA006025 (SEQ ID NO:4).

As shown in Table 2 below and in FIG. 5, the peak LOD score of the mapping is 70.93 (significant threshold is 2.2) and 84% phenotypic variation of the mapping population can be explained by this gene. Table 2, column 1 shows the relative genetic position starting from marker NHA002903 on LG16 in centimorgans (cM), column 2 shows the locus, column 3 shows the LOD score, and column 4 shows the percentage of phenotypic variation of the mapping population.

TABLE 2

| Position (cM) | Locus | LOD | % Expl. |
|---|---|---|---|
| 0.00 | NHA002903 | 0.45 | 1.2 |
| 1.00 | | 0.53 | 1.4 |
| 2.00 | | 0.61 | 1.6 |
| 3.00 | | 0.72 | 1.8 |
| 4.00 | | 0.83 | 2.1 |
| 5.00 | | 0.96 | 2.5 |
| 6.00 | | 1.11 | 2.8 |
| 7.00 | | 1.28 | 3.3 |
| 8.00 | | 1.47 | 3.7 |
| 9.00 | | 1.68 | 4.2 |
| 10.00 | | 1.91 | 4.8 |
| 11.00 | | 2.16 | 5.4 |
| 12.00 | | 2.43 | 6.1 |
| 13.00 | | 2.71 | 6.8 |
| 14.00 | | 3.01 | 7.5 |
| 15.00 | | 3.33 | 8.2 |
| 16.00 | | 3.65 | 9 |
| 17.00 | | 3.97 | 9.8 |
| 18.00 | | 4.29 | 10.5 |
| 19.00 | | 4.6 | 11.2 |
| 20.00 | | 4.91 | 11.9 |
| 21.00 | | 5.2 | 12.6 |
| 22.00 | | 5.48 | 13.2 |
| 23.00 | | 5.74 | 13.8 |
| 24.00 | | 5.98 | 14.3 |
| 24.11 | NHA002966 | 6 | 14.4 |
| 25.11 | | 6.49 | 15.5 |
| 26.11 | | 6.98 | 16.5 |
| 27.11 | | 7.47 | 17.6 |
| 28.11 | | 7.94 | 18.6 |
| 29.11 | | 8.36 | 19.4 |
| 30.11 | | 8.72 | 20.2 |
| 31.11 | | 9.02 | 20.8 |
| 32.11 | | 9.23 | 21.2 |
| 33.11 | | 9.36 | 21.5 |
| 34.01 | NHA003004 | 9.4 | 21.6 |
| 35.01 | | 9.97 | 22.7 |
| 36.01 | | 10.47 | 23.7 |
| 37.01 | | 10.88 | 24.5 |
| 38.01 | | 11.18 | 25.1 |
| 39.01 | | 11.39 | 25.5 |
| 40.01 | | 11.49 | 25.7 |
| 41.01 | | 11.49 | 25.7 |
| 42.01 | | 11.42 | 25.6 |
| 43.01 | | 11.27 | 25.3 |
| 43.35 | NHA006000 | 11.2 | 25.2 |
| 44.35 | | 12.02 | 26.7 |
| 44.50 | NHA005996 | 12.1 | 26.9 |
| 45.50 | | 13.6 | 29.7 |

TABLE 2-continued

| Position (cM) | Locus | LOD | % Expl. |
|---|---|---|---|
| 45.62 | NHA005999 | 13.7 | 29.8 |
| 46.62 | | 13.91 | 30.2 |
| 47.62 | | 13.78 | 30 |
| 47.90 | NHA003041 | 13.68 | 29.8 |
| 48.20 | NHA006001 | 13.69 | 29.8 |
| 49.20 | | 15.35 | 32.8 |
| 50.20 | | 17.19 | 35.9 |
| 51.20 | | 19.2 | 39.1 |
| 52.20 | | 21.36 | 42.5 |
| 53.20 | | 23.64 | 45.8 |
| 54.20 | | 25.99 | 48.9 |
| 55.20 | | 28.32 | 51.9 |
| 56.20 | | 30.54 | 54.6 |
| 57.20 | | 32.55 | 56.9 |
| 58.20 | | 34.24 | 58.8 |
| 59.20 | | 35.54 | 60.1 |
| 60.20 | | 36.4 | 61 |
| 60.76 | NHA006012 | 36.68 | 61.3 |
| 60.76 | NHA003061 | 36.68 | 61.3 |
| 61.76 | | 42.8 | 67 |
| 62.76 | | 48.05 | 71.2 |
| 63.76 | | 51.25 | 73.4 |
| 64.14 | NHA006019 | 51.75 | 73.8 |
| 65.14 | | 61.45 | 79.6 |
| 66.14 | | 68.19 | 82.9 |
| 66.51 | NHA003066 | 69.27 | 83.3 |
| 67.41 | NHA006022 | 70.22 | 83.7 |
| 68.41 | | 70.93 | 84 |
| 69.41 | | 67.25 | 82.4 |
| 70.41 | | 60.09 | 78.9 |
| 71.41 | | 51.44 | 73.6 |
| 72.41 | | 42.92 | 67.1 |
| 72.61 | NHA006025 | 41.26 | 65.6 |
| 73.17 | NHA003071 | 38.65 | 63.2 |
| 73.17 | NHA003070 | 38.65 | 63.2 |
| 74.17 | | 37.76 | 62.3 |
| 75.17 | | 35.7 | 60.3 |
| 76.17 | | 32.58 | 57 |
| 77.17 | | 28.71 | 52.4 |
| 78.17 | | 24.52 | 47 |
| 79.17 | | 20.42 | 41 |
| 79.26 | NHA003075 | 20.09 | 40.5 |
| 80.26 | | 18.36 | 37.8 |
| 81.26 | | 15.69 | 33.4 |
| 82.01 | NHA003074 | 13.4 | 29.3 |

As demonstrated herein, the white seed color gene, mutant allele NSMA, a dominant trait, was mapped to an interval of 5.2 centimorgan (cM) on LG16 and was tightly linked to flanking SNP markers NHA006022 (SEQ ID NO:1) and NHA006025 (SEQ ID NO:2). NHA006022 and NHA006025 are "flanking markers" meaning that they are the closest markers identified on either side of the white seed color gene, NSMA. Therefore, when individuals that carry the white seed color gene SNP profile for NHA006022 and NHA006025 are identified, there is over 99% certainty that the NSMA allele is between those two markers and therefore present in the individual tested, making the SNP markers a very powerful selection tool. Since the SNP markers NHA006022 and NHA006025 are flanking, one could identify the sequence of NSMA by sequencing the interval between the two SNPs.

The mapping results for NSMA presented herein will greatly facilitate white seed sunflower breeding through marker-assisted breeding/selection. Additionally, it is desirable to have a dominant allele conferring white seed color to sunflower, such as mutant allele NSMA, which is easy to transfer to different genetic backgrounds and confers expression of white seed color in hybrid sunflower combinations and their progeny. A unique confectionary sunflower seed color, such as white, aids with seed sorting and breeding. Further, certain consumers find white sunflower seeds more desirable than the black and white striped confectionary sunflower seeds currently available in the market.

Further Embodiments of the Invention

Sunflower is an important and valuable vegetable crop. Thus, a continuing goal of sunflower plant breeders is to develop stable, high yielding hybrid sunflowers that are agronomically sound. To accomplish this goal, the sunflower breeder must select and develop sunflower plants with traits that result in superior cultivars.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer for special advertising and marketing, altered seed and commercial production practices, and new product utilization. The testing preceding release of a new cultivar should take into consideration research and development costs, as well as technical superiority of the final cultivar. For seed-propagated cultivars, it must be feasible to produce seed easily and economically.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, the overall value of the advanced breeding lines, and the number of successful cultivars produced per unit of input (e.g., per year, per dollar expended, etc.).

Promising advanced breeding lines are thoroughly tested and compared to appropriate standards in environments representative of the commercial target area(s) for at least three years. The best lines are candidates for new commercial cultivars. Those still deficient in a few traits are used as parents to produce new populations for further selection.

These processes, which lead to the final step of marketing and distribution, usually take from ten to twenty years from the time the first cross or selection is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of sunflower plant breeding is to develop new, unique, and superior hybrid sunflowers. The breeder initially selects and crosses two or more parental lines, followed by repeated selfing and selection, producing many new genetic combinations. The breeder can theoretically generate billions of different genetic combinations via crossing, selfing, and mutations. The breeder has no direct control at the cellular level. Therefore, two breeders will never develop the same line, or even very similar lines, having the same sunflower traits.

Each year, the plant breeder selects the germplasm to advance to the next generation. This germplasm is grown under different geographical, climatic, and soil conditions, and further selections are then made during, and at the end of, the growing season. The cultivars that are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop superior hybrid sunflowers.

The development of commercial hybrid sunflowers requires the development of sunflower varieties, the crossing of these varieties, and the evaluation of the crosses. Pedigree breeding and recurrent selection breeding methods are used to develop cultivars from breeding populations. Breeding programs combine desirable traits from two or more varieties or various broad-based sources into breeding pools from which cultivars are developed by selfing and selection of desired phenotypes. The new cultivars are crossed with other varieties and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population. Then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines with each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen (Molecular Linkage Map of Soybean (*Glycine max*), pp. 6.131-6.138 in S. J. O'Brien (ed.) *Genetic Maps: Locus Maps of Complex Genomes*, Cold Spring Harbor Laboratory Press, Cold Spring Harbor, N.Y. (1993)) developed a molecular genetic linkage map that consisted of 25 linkage groups with about 365 RFLP, 11 RAPD, three classical markers, and four isozyme loci. See also, Shoemaker, R. C., RFLP Map of Soybean, pp. 299-309, in Phillips, R. L. and Vasil, I. K. (eds.), *DNA-Based Markers in Plants*, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. Diwan, N. and Cregan, P. B., *Theor. Appl. Genet.*, 95:22-225 (1997). SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. A gene of interest directly causes production of protein(s) or RNA that produce a desired trait or phenotype, such as seed color, whereas markers are genetically linked to the gene of interest. If the gene of interest is not known, markers linked to the gene of interest can be used to select for individuals with desirable alleles of the gene of interest. Differences in DNA sequences near the gene of interest can be used as markers to locate the gene and track the desired results in breeding programs. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Flanking markers that are tightly linked to target genes can be used for selection and are sometimes more efficient than direct selection for the target genes. Use of flanking markers on either side of the locus of interest during marker assisted selection increases the probability that the desired gene is selected. Molecular markers may also be used to identify and exclude certain sources of germplasm as parental varieties or ancestors of a plant by providing a means of tracking genetic profiles through crosses.

Mutation breeding is another method of introducing new traits into sunflower varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company (1993).

The production of double haploids can also be used for the development of homozygous varieties in a breeding program. Double haploids are produced by the doubling of a set of chromosomes from a heterozygous plant to produce a completely homozygous individual. For example, see Wan, et al., *Theor. Appl. Genet.*, 77:889-892 (1989).

Descriptions of other breeding methods that are commonly used for different traits and crops can be found in one of several reference books (e.g., *Principles of Plant Breeding*, John Wiley and Son, pp. 115-161 (1960); Allard (1960); Simmonds (1979); Sneep, et al. (1979); Fehr (1987); "Carrots and Related Vegetable *Umbelliferae*," Rubatzky, V. E., et al. (1999).

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Any DNA sequences, whether from a different species or from the same species, which are introduced into the genome using transformation or various breeding methods, are referred to herein collectively as "transgenes." Over the last fifteen to twenty years, several methods for producing transgenic plants have been developed, and the present invention, in particular embodiments, also relates to transformed versions of the claimed line.

Nucleic acids or polynucleotides refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

Plant transformation involves the construction of an expression vector that will function in plant cells. Such a vector comprises DNA comprising a gene under control of, or operatively linked to, a regulatory element (for example, a promoter). The expression vector may contain one or more such operably linked gene/regulatory element combinations. The vector(s) may be in the form of a plasmid, and can be used alone or in combination with other plasmids, to provide transformed sunflower plants using transformation methods as described below to incorporate transgenes into the genetic material of the sunflower plant(s).

Expression Vectors for Sunflower Transformation: Marker Genes

Expression vectors include at least one genetic marker, operably linked to a regulatory element (for example, a promoter) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or an herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley, et al., *PNAS,* 80:4803 (1983). Another commonly used selectable marker gene is the hygromycin phosphotransferase gene which confers resistance to the antibiotic hygromycin. Vanden Elzen, et al., *Plant Mol. Biol.,* 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford, et al., *Plant Physiol.,* 86:1216 (1988); Jones, et al., *Mol. Gen. Genet.,* 210:86 (1987); Svab, et al., *Plant Mol. Biol.,* 14:197 (1990); Hille, et al., *Plant Mol. Biol.,* 7:171 (1986). Other selectable marker genes confer resistance to herbicides such as glyphosate, glufosinate, or bromoxynil. Comai, et al., *Nature,* 317:741-744 (1985); Gordon-Kamm, et al., *Plant Cell,* 2:603-618 (1990); and Stalker, et al., *Science,* 242:419-423 (1988).

Selectable marker genes for plant transformation that are not of bacterial origin include, for example, mouse dihydrofolate reductase, plant 5-enolpyruvylshikimate-3-phosphate synthase, and plant acetolactate synthase. Eichholtz, et al., *Somatic Cell Mol. Genet.,* 13:67 (1987); Shah, et al., *Science,* 233:478 (1986); and Charest, et al., *Plant Cell Rep.,* 8:643 (1990).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include α-glucuronidase (GUS), α-galactosidase, luciferase and chloramphenicol, acetyltransferase. Jefferson, R. A., *Plant Mol. Biol.,* 5:387 (1987); Teeri, et al., *EMBO J.,* 8:343 (1989); Koncz, et al., *PNAS,* 84:131 (1987); and DeBlock, et al., *EMBO J.,* 3:1681 (1984).

In vivo methods for visualizing GUS activity that do not require destruction of plant tissues are available. Molecular Probes, Publication 2908, IMAGENE GREEN, pp. 1-4 (1993) and Naleway, et al., *J. Cell Biol.,* 115:151a (1991). However, these in vivo methods for visualizing GUS activity have not proven useful for recovery of transformed cells because of low sensitivity, high fluorescent backgrounds, and limitations associated with the use of luciferase genes as selectable markers.

More recently, a gene encoding Green Fluorescent Protein (GFP) has been utilized as a marker for gene expression in prokaryotic and eukaryotic cells. Chalfie, et al., *Science,* 263:802 (1994). GFP and mutants of GFP may be used as screenable markers.

Expression Vectors for Sunflower Transformation: Promoters

Genes included in expression vectors must be driven by a nucleotide sequence comprising a regulatory element (for example, a promoter). Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters which initiate transcription only in certain tissue are referred to as "tissue-specific." A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters:

An inducible promoter is operably linked to a gene for expression in sunflower. Optionally, the inducible promoter is operably linked to a nucleotide sequence encoding a signal sequence which is operably linked to a gene for expression in sunflower. With an inducible promoter, the rate of transcription increases in response to an inducing agent.

Any inducible promoter can be used in the instant invention. See Ward, et al., *Plant Mol. Biol.,* 22:361-366 (1993). Exemplary inducible promoters include, but are not limited to, that from the ACEI system which responds to copper (Meft, et al., *PNAS,* 90:4567-4571 (1993)); In2 gene from maize which responds to benzenesulfonamide herbicide safeners (Hershey, et al., *Mol. Gen. Genet.,* 227:229-237 (1991) and Gatz, et al., *Mol. Gen. Genet.,* 243:32-38 (1994)) or Tet repressor from Tn10 (Gatz, et al., *Mol. Gen. Genet.,* 227:229-237 (1991)). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena, et al., *PNAS,* 88:0421 (1991).

B. Constitutive Promoters:

A constitutive promoter is operably linked to a gene for expression in sunflower or the constitutive promoter is operably linked to a nucleotide sequence encoding a signal sequence which is operably linked to a gene for expression in sunflower.

Many different constitutive promoters can be utilized in the instant invention. Exemplary constitutive promoters include, but are not limited to, the promoters from plant viruses such as the 35S promoter from CaMV (Odell, et al., *Nature,* 313:810-812 (1985)) and the promoters from such genes as rice actin (McElroy, et al., *Plant Cell,* 2:163-171 (1990)); ubiquitin (Christensen, et al., *Plant Mol. Biol.,* 12:619-632 (1989) and Christensen, et al., *Plant Mol. Biol.,* 18:675-689 (1992)); pEMU (Last, et al., *Theor. Appl. Genet.,* 81:581-588 (1991)); MAS (Velten, et al., *EMBO J.,* 3:2723-2730 (1984)) and maize H3 histone (Lepetit, et al., *Mol. Gen. Genet.,* 231:276-285 (1992) and Atanassova, et al., *Plant J.,* 2 (3):291-300 (1992)). The ALS promoter, Xba1/Nco1 fragment 5' to the *Brassica napus* ALS3 structural gene (or a nucleotide sequence similarity to said Xba1/Nco1 fragment), represents a particularly useful constitutive promoter. See PCT Application No. WO 96/30530.

C. Tissue-Specific or Tissue-Preferred Promoters:

A tissue-specific promoter is operably linked to a gene for expression in sunflower. Optionally, the tissue-specific promoter is operably linked to a nucleotide sequence encoding a signal sequence which is operably linked to a gene for expression in sunflower. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai, et al., Science, 23:476-482 (1983) and Sengupta-Gopalan, et al., PNAS, 82:3320-3324 (1985)); a leaf-specific and light-induced promoter such as that from cab or rubisco (Simpson, et al., EMBO J., 4(11):2723-2729 (1985) and Timko, et al., Nature, 318:579-582 (1985)); an anther-specific promoter such as that from LAT52 (Twell, et al., Mol. Gen. Genet., 217:240-245 (1989)); a pollen-specific promoter such as that from Zm13 (Guerrero, et al., Mol. Gen. Genet., 244:161-168 (1993)) or a microspore-preferred promoter such as that from apg (Twell, et al., Sex. Plant Reprod., 6:217-224 (1993)).

Signal Sequences for Targeting Proteins to Subcellular Compartments

Transport of protein produced by transgenes to a subcellular compartment such as the chloroplast, vacuole, peroxisome, glyoxysome, cell wall, or mitochondrion, or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example, Becker, et al., Plant Mol. Biol., 20:49 (1992); Close, P. S., Master's Thesis, Iowa State University (1993); Knox, C., et al., "Structure and Organization of Two Divergent Alpha-Amylase Genes from Barley," Plant Mol. Biol., 9:3-17 (1987); Lerner, et al., Plant Physiol., 91:124-129 (1989); Fontes, et al., Plant Cell, 3:483-496 (1991); Matsuoka, et al., PNAS, 88:834 (1991); Gould, et al., J. Cell. Biol., 108:1657 (1989); Creissen, et al., Plant J., 2:129 (1991); Kalderon, et al., A short amino acid sequence able to specify nuclear location, Cell, 39:499-509 (1984); and Steifel, et al., Expression of a maize cell wall hydroxyproline-rich glycoprotein gene in early leaf and root vascular differentiation, Plant Cell, 2:785-793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem., 114:92-6 (1981).

According to a preferred embodiment, the transgenic plant provided for commercial production of foreign protein is sunflower. In another preferred embodiment, the biomass of interest is seed. For the relatively small number of transgenic plants that show higher levels of expression, a genetic map can be generated, primarily via conventional RFLP, PCR, and SSR analysis, which identifies the approximate chromosomal location of the integrated DNA molecule. For exemplary methodologies in this regard, see Methods in Plant Molecular Biology and Biotechnology, Glick and Thompson Eds., 269:284, CRC Press, Boca Raton (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR, and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

A. Genes that Confer Resistance to Pests or Disease and that Encode:

1. Plant disease resistance genes. Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains. See, for example, Jones, et al., Science, 266:789 (1994) (cloning of the tomato Cf-9 gene for resistance to *Cladosporium fulvum*); Martin, et al., Science, 262:1432 (1993) (tomato Pto gene for resistance to *Pseudomonas syringae* pv. tomato encodes a protein kinase); and Mindrinos, et al., Cell, 78:1089 (1994) (*Arabidopsis* RSP2 gene for resistance to *Pseudomonas syringae*).

2. A *Bacillus thuringiensis* protein, a derivative thereof, or a synthetic polypeptide modeled thereon. See, for example, Geiser, et al., Gene, 48:109 (1986), who disclose the cloning and nucleotide sequence of a Bt δ-endotoxin gene. Moreover, DNA molecules encoding δ-endotoxin genes can be purchased from American Type Culture Collection, Manassas, Va., for example, under ATCC Accession Nos. 40098, 67136, 31995, and 31998.

3. A lectin. See, for example, the disclosure by Van Damme, et al., *Plant Mol. Biol.*, 24:25 (1994), who disclose the nucleotide sequences of several *Clivia miniata* mannose-binding lectin genes.

4. A vitamin-binding protein such as avidin. See PCT Application No. US 93/06487, the contents of which are hereby incorporated by reference. The application teaches the use of avidin and avidin homologues as larvicides against insect pests.

5. An enzyme inhibitor, for example, a protease or proteinase inhibitor, or an amylase inhibitor. See, for example, Abe, et al., *J. Biol. Chem.*, 262:16793 (1987) (nucleotide sequence of rice cysteine proteinase inhibitor); Huub, et al., *Plant Mol. Biol.*, 21:985 (1993) (nucleotide sequence of cDNA encoding tobacco proteinase inhibitor I); and Sumitani, et al., *Biosci. Biotech. Biochem.*, 57:1243 (1993) (nucleotide sequence of *Streptomyces nitrosporeus* α-amylase inhibitor).

6. An insect-specific hormone or pheromone, such as an ecdysteroid and juvenile hormone, a variant thereof, a mimetic based thereon, or an antagonist or agonist thereof. See, for example, the disclosure by Hammock, et al., *Nature*, 344:458 (1990), of baculovirus expression of cloned juvenile hormone esterase, an inactivator of juvenile hormone.

7. An insect-specific peptide or neuropeptide which, upon expression, disrupts the physiology of the affected pest. For example, see the disclosures of Regan, *J. Biol. Chem.*, 269:9 (1994) (expression cloning yields DNA coding for insect diuretic hormone receptor) and Pratt, et al., *Biochem. Biophys. Res. Comm.*, 163:1243 (1989) (an allostatin is identified in *Diploptera puntata*). See also, U.S. Pat. No. 5,266, 317 to Tomalski, et al., who disclose genes encoding insect-specific, paralytic neurotoxins.

8. An insect-specific venom produced in nature, by a snake, a wasp, etc. For example, see Pang, et al., *Gene*, 116:165 (1992), for disclosure of heterologous expression in plants of a gene coding for a scorpion insectotoxic peptide.

9. An enzyme responsible for a hyper-accumulation of a monoterpene, a sesquiterpene, a steroid, hydroxamic acid, a phenylpropanoid derivative, or another non-protein molecule with insecticidal activity.

10. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See PCT Application No. WO 93/02197 in the name of Scott, et al., which discloses the nucleotide sequence of a callase gene. DNA molecules which contain chitinase-encoding sequences can be obtained, for example, from the ATCC under Accession Nos. 39637 and 67152. See also, Kramer, et al., *Insect Biochem. Mol. Biol.*, 23:691 (1993), who teach the nucleotide sequence of a cDNA encoding tobacco hornworm chitinase, and Kawalleck, et al., *Plant Mol. Biol.*, 21:673 (1993), who provide the nucleotide sequence of the parsley ubi4-2 polyubiquitin gene.

11. A molecule that stimulates signal transduction. For example, see the disclosure by Botella, et al., *Plant Mol. Biol.*, 24:757 (1994), of nucleotide sequences for mung bean calmodulin cDNA clones, and Griess, et al., *Plant Physiol.*, 104:1467 (1994), who provide the nucleotide sequence of a maize calmodulin cDNA clone.

12. A hydrophobic moment peptide. See PCT Application No. WO 95/16776 (disclosure of peptide derivatives of tachyplesin which inhibit fungal plant pathogens) and PCT Application No. WO 95/18855 (teaches synthetic antimicrobial peptides that confer disease resistance), the respective contents of which are hereby incorporated by reference.

13. A membrane permease, a channel former, or a channel blocker. For example, see the disclosure of Jaynes, et al., *Plant Sci.*, 89:43 (1993), of heterologous expression of a cecropin-β, lytic peptide analog to render transgenic tobacco plants resistant to *Pseudomonas solanacearum*.

14. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy, et al., *Ann. Rev. Phytopathol.*, 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. Id.

15. An insect-specific antibody or an immunotoxin derived therefrom. Thus, an antibody targeted to a critical metabolic function in the insect gut would inactivate an affected enzyme, killing the insect. See Taylor, et al., Abstract #497, Seventh Int'l Symposium on Molecular Plant-Microbe Interactions, Edinburgh, Scotland (1994) (enzymatic inactivation in transgenic tobacco via production of single-chain antibody fragments).

16. A virus-specific antibody. See, for example, Tavladoraki, et al., *Nature*, 366:469 (1993), who show that transgenic plants expressing recombinant antibody genes are protected from virus attack.

17. A developmental-arrestive protein produced in nature by a pathogen or a parasite. Thus, fungal endo-α-1, 4-D-polygalacturonases facilitate fungal colonization and plant nutrient released by solubilizing plant cell wall homo-α-1, 4-D-galacturonase. See Lamb, et al., *Bio/technology*, 10:1436 (1992). The cloning and characterization of a gene which encodes a bean endopolygalacturonase-inhibiting protein is described by Toubart, et al., *Plant J.*, 2:367 (1992).

18. A developmental-arrestive protein produced in nature by a plant. For example, Logemann, et al., *Bio/technology*, 10:305 (1992), have shown that transgenic plants expressing the barley ribosome-inactivating gene have an increased resistance to fungal disease.

Any of the above listed disease or pest resistance genes (1-18) can be introduced into the claimed sunflowers through a variety of means including but not limited to transformation and crossing.

B. Genes that Confer Resistance to an Herbicide:

1. An herbicide that inhibits the growing point or meristem, such as an imidazolinone or a sulfonylurea. Exemplary genes in this category code for mutant ALS and AHAS enzyme as described, for example, by Lee, et al., *EMBO J.*, 7:1241 (1988) and Miki, et al., *Theor. Appl. Genet.*, 80:449 (1990), respectively.

2. Glyphosate (resistance conferred by mutant 5-enolpyruvylshikimate-3-phosphate synthase (EPSPS) and aroA genes, respectively) and other phosphono compounds, such as glufosinate (phosphinothricin acetyl transferase (PAT), dicamba and *Streptomyces hygroscopicus* phosphinothricin-acetyl transferase PAT bar genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. A DNA molecule encoding a mutant aroA gene can be obtained under ATCC Accession No. 39256, and the nucleotide sequence of the mutant gene is disclosed in U.S. Pat. No. 4,769,061 to Comai. See also, Umaballava-Mobapathie in *Transgenic Research*, 8:1, 33-44 (1999) that discloses *Lactuca sativa* resistant to glufosinate. European Patent Application No. 0 333 033 to Kumada, et al., and U.S. Pat. No. 4,975,374 to Goodman, et al., disclose nucleotide sequences of glutamine synthetase genes which confer resistance to herbicides, such as L-phosphinothricin. The nucleotide sequence of a phosphinothricin-acetyl-transferase gene is provided in European Application No. 0 242 246 to Leemans, et al. DeGreef, et al., *Bio/technology*, 7:61 (1989), describe the production of transgenic plants that express chimeric bar genes coding for phosphinothricin acetyl transferase activity. Exemplary of genes conferring resistance to phenoxy proprionic acids and cyclohexones, such as sethoxydim and haloxyfop, are the Acc1-S1, Acc1-S2, and Acc1-S3 genes described by Marshall, et al., *Theor. Appl. Genet.,* 83:435 (1992).

3. An herbicide that inhibits photosynthesis, such as a triazine (psbA and gs+ genes) and a benzonitrile (nitrilase gene). Przibilla, et al., *Plant Cell,* 3:169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes, et al., *Biochem. J.,* 285:173 (1992).

4. Acetohydroxy acid synthase, which has been found to make plants that express this enzyme resistant to multiple types of herbicides, has been introduced into a variety of plants. See Hattori, et al., *Mol. Gen. Genet.,* 246:419 (1995). Other genes that confer tolerance to herbicides include a gene encoding a chimeric protein of rat cytochrome P4507A1 and yeast NADPH-cytochrome P450 oxidoreductase (Shiota, et al., *Plant Physiol.,* 106:17 (1994)), genes for glutathione reductase and superoxide dismutase (Aono, et al., *Plant Cell Physiol.,* 36:1687 (1995)), and genes for various phosphotransferases (Datta, et al., *Plant Mol. Biol.,* 20:619 (1992)).

5. Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306, 6,282,837, 5,767,373, and International Publication WO 01/12825.

Any of the above listed herbicide genes (1-5) can be introduced into the claimed sunflowers through a variety of means including, but not limited to, transformation and crossing.

C. Genes that Confer or Contribute to a Value-Added Trait, Such as:

1. Increased iron content of the sunflower, for example, by introducing into a plant a soybean ferritin gene as described in Goto, et al., *Acta Horticulturae.,* 521, 101-109 (2000).

2. Decreased nitrate content of leaves, for example, by introducing into a sunflower a gene coding for a nitrate reductase. See, for example, Curtis, et al., *Plant Cell Rep.,* 18:11, 889-896 (1999).

3. Modified fatty acid metabolism, for example, by introducing into a plant an antisense gene of stearyl-ACP desaturase to increase stearic acid content of the plant. See Knultzon, et al., *PNAS,* 89:2625 (1992).

4. Modified carbohydrate composition effected, for example, by introducing into plants a gene coding for an enzyme that alters the branching pattern of starch. See Shiroza, et al., *J. Bacteriol.,* 170:810 (1988) (nucleotide sequence of *Streptococcus mutants* fructosyltransferase gene); Steinmetz, et al., *Mol. Gen. Genet.,* 20:220 (1985) (nucleotide sequence of *Bacillus subtilis* levansucrase gene); Pen, et al., *Bio/technology,* 10:292 (1992) (production of transgenic plants that express *Bacillus licheniformis* α-amylase); Elliot, et al., *Plant Mol. Biol.,* 21:515 (1993) (nucleotide sequences of tomato invertase genes); Søgaard, et al., *J. Biol. Chem.,* 268:22480 (1993) (site-directed mutagenesis of barley α-amylase gene); and Fisher, et al., *Plant Physiol.,* 102:1045 (1993) (maize endosperm starch branching enzyme II).

D. Genes that Control Male-Sterility:

1. Introduction of a deacetylase gene under the control of a tapetum-specific promoter and with the application of the chemical N-Ac-PPT. See International Publication WO 01/29237.

2. Introduction of various stamen-specific promoters. See International Publications WO 92/13956 and WO 92/13957.

3. Introduction of the barnase and the barstar genes. See Paul, et al., *Plant Mol. Biol.,* 19:611-622 (1992).

For additional examples of nuclear male and female sterility systems and genes, see also, U.S. Pat. Nos. 5,859,341, 6,297,426, 5,478,369, 5,824,524, 5,850,014 and 6,265,640. See also Hanson, Maureen R., et. al., (2004) "Interactions of Mitochondrial and Nuclear Genes That Affect Male Gametophyte Development" *Plant Cell.* 16:S154-S169, all of which are hereby incorporated by reference.

Methods for Sunflower Transformation

Numerous methods for plant transformation have been developed, including biological and physical, plant transformation protocols. See, for example, Miki, et al., "Procedures for Introducing Foreign DNA into Plants" in *Methods in Plant Molecular Biology and Biotechnology,* Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in *Methods in Plant Molecular Biology and Biotechnology,* Glick and Thompson Eds., CRC Press, Inc., Boca Raton, pp. 89-119 (1993).

A. *Agrobacterium*-Mediated Transformation:

One method for introducing an expression vector into plants is based on the natural transformation system of *Agrobacterium.* See, for example, Horsch, et al., *Science,* 227:1229 (1985); Curtis, et al., *Journal of Experimental Botany,* 45:279, 1441-1449 (1994); Tones, et al., *Plant Cell Tissue and Organ Culture,* 34:3, 279-285 (1993); and Dinant, et al., *Molecular Breeding,* 3:1, 75-86 (1997). *A. tumefaciens* and *A. rhizogenes* are plant pathogenic soil bacteria which genetically transform plant cells. The Ti and Ri plasmids of *A. tumefaciens* and *A. rhizogenes,* respectively, carry genes responsible for genetic transformation of the plant. See, for example, Kado, C. I., *Crit. Rev. Plant Sci.,* 10:1 (1991). Descriptions of *Agrobacterium* vector systems and methods for *Agrobacterium*-mediated gene transfer are provided by Gruber, et al., supra, Miki, et al., supra, and Moloney, et al., *Plant Cell Rep.,* 8:238 (1989). See also, U.S. Pat. No. 5,591,616 issued Jan. 7, 1997.

B. Direct Gene Transfer:

Several methods of plant transformation collectively referred to as direct gene transfer have been developed as an alternative to *Agrobacterium*-mediated transformation. A generally applicable method of plant transformation is microprojectile-mediated transformation wherein DNA is carried on the surface of microprojectiles measuring 1 μm to 4 μm. The expression vector is introduced into plant tissues with a biolistic device that accelerates the microprojectiles to speeds of 300 m/s to 600 m/s which is sufficient to penetrate plant cell walls and membranes. Russell, D. R., et al., *Plant Cell Rep.,* 12 (3, January), 165-169 (1993); Aragao, F. J. L., et al., *Plant Mol. Biol.,* 20 (2, October), 357-359 (1992); Aragao, F. J. L., et al., *Plant Cell Rep.,* 12 (9, July), 483-490 (1993); Aragao, *Theor. Appl. Genet.,* 93:142-150 (1996); Kim, J., Minamikawa, T., *Plant Sci.,* 117:131-138 (1996); Sanford, et al., *Part. Sci. Technol.,* 5:27 (1987); Sanford, J. C., *Trends Biotech.,* 6:299 (1988); Klein, et al.,

*Bio/technology,* 6:559-563 (1988); Sanford, J. C., *Physiol. Plant,* 7:206 (1990); Klein, et al., *Bio/technology,* 10:268 (1992).

Another method for physical delivery of DNA to plants is sonication of target cells. Zhang, et al., *Bio/technology,* 9:996 (1991). Alternatively, liposome and spheroplast X4237 have been used to introduce expression vectors into plants. Deshayes, et al., *EMBO J.,* 4:2731 (1985) and Christou, et al., *PNAS,* 84:3962 (1987). Direct uptake of DNA into protoplasts using $CaCl_2$ precipitation, polyvinyl alcohol, or poly-L-ornithine has also been reported. Hain, et al., *Mol. Gen. Genet.,* 199:161 (1985) and Draper, et al., *Plant Cell Physiol.,* 23:451 (1982). Electroporation of protoplasts and whole cells and tissues have also been described. Saker, M., Kuhne, T., *Biologia Plantarum,* 40(4): 507-514 (1997/98); Donn, et al., In Abstracts of VIIth International Congress on Plant Cell and Tissue Culture IAPTC, A2-38, p. 53 (1990); D'Halluin, et al., *Plant Cell,* 4:1495-1505 (1992); and Spencer, et al., *Plant Mol. Biol.,* 24:51-61 (1994). See also Chupean, et al., *Bio/technology,* 7:5, 503-508 (1989).

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformed plants obtained with the protoplasm of the invention are intended to be within the scope of this invention.

Following transformation of sunflower target tissues, expression of the above-described selectable marker genes allows for preferential selection of transformed cells, tissues and/or plants, using regeneration and selection methods now well known in the art.

The foregoing methods for transformation would typically be used for producing a transgenic line. The transgenic line could then be crossed with another (non-transformed or transformed) line in order to produce a new transgenic sunflower line. Alternatively, a genetic trait which has been engineered into a particular sunflower using the foregoing transformation techniques could be introduced into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

Gene Conversions

When the term "sunflower plant" is used in the context of the present invention, this also includes any gene conversions of that variety. The term "gene converted plant" as used herein refers to those sunflower plants which are developed by backcrossing, genetic engineering, or mutation, wherein essentially all of the desired morphological and physiological characteristics of a variety are recovered in addition to the one or more genes transferred into the variety via the backcrossing technique, genetic engineering, or mutation. Backcrossing methods can be used with the present invention to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, 9, or more times to the recurrent parent. The parental sunflower plant which contributes the gene for the desired characteristic is termed the "nonrecurrent" or "donor parent." This terminology refers to the fact that the nonrecurrent parent is used one time in the backcross protocol and therefore does not recur. The parental sunflower plant to which the gene or genes from the nonrecurrent parent are transferred is known as the recurrent parent as it is used for several rounds in the backcrossing protocol. Poehlman & Sleper (1994) and Fehr (1993). In a typical backcross protocol, the original variety of interest (recurrent parent) is crossed to a second variety (nonrecurrent parent) that carries the gene of interest to be transferred. The resulting progeny from this cross are then crossed again to the recurrent parent and the process is repeated until a sunflower plant is obtained wherein essentially all of the desired morphological and physiological characteristics of the recurrent parent are recovered in the converted plant, in addition to the transferred gene from the nonrecurrent parent.

The selection of a suitable recurrent parent is an important step for a successful backcrossing procedure. The goal of a backcross protocol is to alter or substitute a trait or characteristic in the original line. To accomplish this, a gene of the recurrent cultivar is modified or substituted with the desired gene from the nonrecurrent parent, while retaining essentially all of the rest of the desired genetic, and therefore the desired physiological and morphological characteristics of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many gene traits have been identified that are not regularly selected in the development of a new line but that can be improved by backcrossing techniques. Gene traits may or may not be transgenic. Examples of these traits include, but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability, and yield enhancement. These genes are generally inherited through the nucleus. Several of these gene traits are described in U.S. Pat. Nos. 5,777,196, 5,948, 957, and 5,969,212, the disclosures of which are specifically hereby incorporated by reference.

Tissue Culture

Further reproduction of the variety can occur by tissue culture and regeneration. Tissue culture of various tissues of sunflower and regeneration of plants therefrom is well known and widely published. For example, reference may be had to Teng, et al., *HortScience,* 27:9, 1030-1032 (1992); Teng, et al., *HortScience,* 28:6, 669-1671 (1993); Zhang, et al., *Journal of Genetics and Breeding,* 46:3, 287-290 (1992); Webb, et al., *Plant Cell Tissue and Organ Culture,* 38:1, 77-79 (1994); Curtis, et al., *Journal of Experimental Botany,* 45:279, 1441-1449 (1994); Nagata, et al., *Journal for the American Society for Horticultural Science,* 125:6, 669-672 (2000); and Ibrahim, et al., *Plant Cell Tissue and Organ Culture,* 28(2), 139-145 (1992). It is clear from the literature that the state of the art is such that these methods of obtaining plants are routinely used and have a high rate of success. Thus, another aspect of this invention is to provide cells which upon growth and differentiation produce sunflower plants having the physiological and morphological characteristics of sunflower plants, parts or seeds having mutant allele NSMA.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques, the disclosures of which are incorporated herein by reference.

Additional Breeding Methods

This invention also is directed to methods for producing a sunflower plant by crossing a first parent sunflower plant with a second parent sunflower plant wherein the first or second parent sunflower plant is a sunflower plant having mutant allele NSMA. Further, both first and second parent sunflower plants can come from a sunflower plant having mutant allele NSMA. Thus, any such methods using a sunflower plant having mutant allele NSMA are part of this invention: selfing, backcrosses, hybrid production, crosses to populations, and the like. All plants produced using a sunflower plant having mutant allele NSMA as at least one parent are within the scope of this invention, including those developed from cultivars derived from a sunflower plant having mutant allele NSMA. Advantageously, this hybrid sunflower could be used in crosses with other, different, sunflower plants to produce the first generation ($F_1$) sunflower hybrid seeds and plants with superior characteristics. The cultivar of the invention can also be used for transformation where exogenous genes are introduced and expressed by the cultivar of the invention. Genetic variants created either through traditional breeding methods using a sunflower plant having mutant allele NSMA or through transformation of a sunflower plant having mutant allele NSMA by any of a number of protocols known to those of skill in the art are intended to be within the scope of this invention.

Additionally, a sunflower plant having mutant allele NSMA can also be used for transformation where exogenous genes are introduced and expressed by the sunflower of the invention. Genetic variants created either through traditional breeding methods using a sunflower plant having mutant allele NSMA or through transformation of a sunflower plant having mutant allele NSMA by any of a number of protocols known to those of skill in the art are intended to be within the scope of this invention.

The following describes breeding methods that may be used with a sunflower plant having mutant allele NSMA in the development of further sunflower plants. One such embodiment is a method for developing inbred sunflower plants having mutant allele NSMA progeny sunflower plants in a sunflower plant breeding program comprising: obtaining the sunflower plant, or a part thereof, of a sunflower plant having mutant allele NSMA, utilizing said plant or plant part as a source of breeding material, and selecting a sunflower plant having mutant allele NSMA progeny plant with molecular markers in common with a sunflower plant having mutant allele NSMA and/or with morphological and/or physiological characteristics of a sunflower plant having mutant allele NSMA, such as white seeds. Breeding steps that may be used in the sunflower plant breeding program include pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

Another method involves producing a population of a sunflower plant having mutant allele NSMA progeny sunflower plants, comprising crossing a sunflower plant having mutant allele NSMA with another sunflower plant, thereby producing a population of sunflower plants, which, on average, derive 50% of their alleles from a sunflower plant having mutant allele NSMA. A plant of this population may be selected and repeatedly selfed or sibbed with a hybrid sunflower resulting from these successive filial generations. One embodiment of this invention is the hybrid sunflower produced by this method and that has obtained at least 50% of its alleles from a sunflower plant having mutant allele NSMA.

One of ordinary skill in the art of plant breeding would know how to evaluate the traits of two plant varieties to determine if there is no significant difference between the two traits expressed by those varieties. For example, see Fehr and Walt, *Principles of Cultivar Development*, pp. 261-286 (1987). Thus the invention includes a sunflower plant having mutant allele NSMA progeny sunflower plants comprising mutant allele NSMA and having white seeds. Using techniques described herein, molecular markers may be used to identify said progeny plant as a sunflower progeny plant having mutant allele NSMA. Mean trait values may be used to determine whether trait differences are significant, and preferably the traits are measured on plants grown under the same environmental conditions. Once such a variety is developed, its value is substantial since it is important to advance the germplasm base as a whole in order to maintain or improve traits such as yield, disease resistance, pest resistance, and plant performance in extreme environmental conditions.

Progeny of a sunflower plant having mutant allele NSMA may also be characterized through their filial relationship with a sunflower plant having mutant allele NSMA, as for example, being within a certain number of breeding crosses of a sunflower plant having mutant allele NSMA. A breeding cross is a cross made to introduce new genetics into the progeny, and is distinguished from a cross, such as a self or a sib cross, made to select among existing genetic alleles. The lower the number of breeding crosses in the pedigree, the closer the relationship between a sunflower plant having mutant allele NSMA and its progeny. For example, progeny produced by the methods described herein may be within 1, 2, 3, 4, or 5 breeding crosses of a sunflower plant having mutant allele NSMA.

As used herein, the term "plant" includes plant cells, plant protoplasts, plant cell tissue cultures from which sunflower plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, stems, and the like.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

DEPOSIT INFORMATION

Deposits of the Nuseed Americas Inc. proprietary sunflower seeds SA425A and X4237 containing mutant allele NSMA of the invention disclosed above and recited in the appended claims have been made with the American Type Culture Collection (ATCC), 10801 University Boulevard, Manassas, Va. 20110 under the terms of the Budapest Treaty. The dates of deposit were Apr. 1, 2016 and Jun. 16, 2016. The deposits of 2,500 seeds each were taken from the same deposits maintained by Nuseed Americas Inc. since prior to the filing date of this application. All restrictions will be irrevocably removed upon granting of a patent, and the deposits are intended to meet all of the requirements of 37 C.F.R. §§1.801-1.809. The ATCC Accession Numbers are PTA-122987 and PTA-123220. The deposits will be maintained in the depository for a period of thirty years, or five years after the last request, or for the enforceable life of the patent, whichever is longer, and will be replaced as necessary during that period.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

What is claimed is:

1. A sunflower plant having white seed color, wherein said white seed color is conferred by mutant allele NSMA.

2. A sunflower seed containing a mutant allele designated NSMA, wherein representative samples of seed containing said allele NSMA were deposited under ATCC Accession Nos. PTA-122987 and PTA-123220.

3. A sunflower plant, or a part thereof, produced by growing the seed of claim 2.

4. A tissue culture produced from protoplasts or cells from the plant of claim 3, wherein said cells or protoplasts are produced from a plant part selected from the group consisting of leaf, pollen, embryo, cotyledon, hypocotyl, meristematic cell root, root tip, pistil, anther, ovule, flower, shoot, stem, seed, and petiole.

5. A sunflower plant regenerated from the tissue culture of claim 4, wherein said plant has mutant allele NSMA, and wherein said mutant allele confers white seed color.

6. A method for producing a hybrid sunflower seed, said method comprising crossing two sunflower plants and harvesting the resultant sunflower seed, wherein at least one sunflower plant is the sunflower plant of claim 3.

7. A hybrid sunflower seed produced by the method of claim 6.

8. A sunflower plant, or a part thereof, produced by growing said hybrid sunflower seed of claim 7, wherein said plant contains mutant allele NSMA, and wherein said mutant allele confers white seed color.

9. A method of producing a sunflower plant wherein said method comprises introducing a transgene into the plant of claim 3.

10. A sunflower plant produced by the method of claim 9.

11. A method for transferring mutant allele NSMA to a different genetic background, wherein the method comprises:

(a) obtaining the hybrid sunflower plant of claim 8;
(b) backcrossing said hybrid plant to a recipient parent plant not having mutant allele NSMA to produce backcross progeny plants;
(c) selecting for backcross progeny plants that contain mutant allele NSMA;
(d) backcrossing said selected backcross progeny plants to said recipient parent;
(e) repeating steps (c) and (d) two or more times in succession to produce selected third or higher backcross progeny plants that contain mutant allele NSMA; and
(f) harvesting the resulting seed.

12. A plant produced from the seed of claim 11, wherein said plant contains mutant allele NSMA and has white colored seeds.

* * * * *